United States Patent [19]

Tinsley et al.

[11] Patent Number: 5,972,609
[45] Date of Patent: Oct. 26, 1999

[54] UTROPHIN GENE PROMOTOR

[75] Inventors: Jonathon Mark Tinsley; Kay Elizabeth Davies, both of Oxford, United Kingdom; Carina Dennis, New York, N.Y.

[73] Assignee: Medical Research Council, London, United Kingdom

[21] Appl. No.: 08/945,296

[22] PCT Filed: Apr. 24, 1996

[86] PCT No.: PCT/GB96/00979

§ 371 Date: Oct. 22, 1997

§ 102(e) Date: Oct. 22, 1997

[87] PCT Pub. No.: WO96/34101

PCT Pub. Date: Oct. 31, 1996

[30] Foreign Application Priority Data

Apr. 24, 1995 [GB] United Kingdom .................... 9508236
Dec. 20, 1995 [GB] United Kingdom .................... 9526028

[51] Int. Cl.$^6$ .............................. C12Q 1/68; C12P 21/00; C12N 5/10; C12N 15/11
[52] U.S. Cl. ............................. 435/6; 435/69.1; 435/325; 536/23.1; 536/24.1
[58] Field of Search ............................... 435/6, 69.1, 325; 536/24.1, 23.1

[56] References Cited

PUBLICATIONS

Hum. Mol. Genet., vol. 2, no. 11, 1993, pp. 1765–1772, Pearce et al.: "The utrophin and dystrophin genes share similarities in genomic structure".

Nature Genetics vol. 6, Mar. 1994, pp. 236–244, Cross et al.: "Purification of CpG islands using a methylated DNA binding column".

Database Strand Embl Empri AN: HS54B8R, Oct. 22, 1995 Mac Donald et al.

Dev Dynamics vol. 198, Dec. 1993, pp. 254–264, Schofield et al.: "Expression of the dystrophin–related protein (utrophine) gene during mouse embryogenesis".

Biotech Business News, vol. 3, No. 72, Jan. 28, 1994, p. 15, Oncogene Sci. Corpo. et al.: "Muscular dystrophy therapy sought".

Nature, vol. 360–593, XP002010740 Tinsley et al.: "Primary structure of dystrophin–related protein".

*Primary Examiner*—John S. Brusca
*Attorney, Agent, or Firm*—Nixon & Vanderhye P.C.

[57] ABSTRACT

Mouse and human utrophin gene promoters are provided. The promoters or fragments and derivatives may be used to control transcription of heterologous sequences, including coding sequences of reporter genes. Expression systems such as host cells containing nucleic acid constructs which comprise a promoter as provided operably linked to a heterologous sequence may be used to screen substances for ability to modulate activity of the utrophin promoter. Substances with such ability may be manufactured and/or used in the preparation of compositions such as medicaments. Up-regulation of utrophin expression may compensate for dystrophin loss in muscular dystrophy patients.

27 Claims, 7 Drawing Sheets

Fig.2.

```
   1  AAGCTTGGAA CAGGCTCTAT AACAGATGTG CGTTTGTGTG TGCATATTGG
      ─────
      HindIII
  51  AAAACAGAAA AATAAGGTCA GCGCAAACAC TACTTGTAAT ACAAACTAAT
 101  GTAAGAGAAA ACTTCTTTTT CAATATTAAC AACGACACTA GAGAAATAAT
 151  GTAAAATAAA TATACGGTTG AACTAGGGG TAAAAAAAAA ATCAGCAACG
 201  TCAGCAAACT GAGATGGGGT GAGTTGGAAG GCAGATTGGA ATTTATCTCT
                                                      AP-1
                                                    ───────
 251  TAACAAAATA TCACCCTAAC TAGAGACCTG TTTTGCCTAA GGGGACGTGA
                             AP-1
                           ───────
 301  CTCACATTTT CGGATAATCT GAATAAGGGG AATTGTGTCT GCTCGAGGCA
      ────                                        ──────
                                                   XhoI
 351  TCCATTCTGG TTCGGTCTCC GGACTCCCGG CTCCCGGCAC GCACGGTTCA
                    AP-2
                 ────────
 401  CTCTGGAGCG CGCGCCCCAG GCCAGCCAAG CGCCGAGCCG GGCTGCTGCG
                                                      Myo D
                                                    ────
 451  GGCTGGGAGG GCGCGCAGGG CCGGCGCTGA TTGACGGGGC GCGCAGTCAG
      ──
 501  GTGACTTGGG GCGCCAAGTT CCCGACGCGG TGGCCGCGGT GACCGCCGAG
 551  GCCCGGCAGA CGCTGACCCG GAACGTAGT GGGGCTGATC TTCCGGAACA
                    ──────  SP1
                    SmaI  ───
 601  AAGTTGCTGG GCCGGCGGCG GCGGGGCGAG AGCGCCGAGG GGGAGCCGGA
 651  GCGCTGCAGA GGCGCGGGCC GGAGGGCTGG CGCTGATCTG CACCCTTCTC
         ──────                                      ──────
         PstI                                         SmaI
 701  ATCTGGAGAG CGGACCCCTG GCTGCCCGGA GGCGAGCCCC TTCCCGGGGG
          SP1
      ────
 751  GTGGGGGCGG CAACGCGCGA CCCAGCGGTC CTGCGCCCCA CCCTCCCTCC
                                                   AP-2
                                                ────────
 801  TCCGCCTCCA GCGCTCGGCT CCAACAAAGG GGCAGGCCCG CAGCGGGGAG
 851  GAGGAGGAGG AGCCGCCGAA GGAGCGAGCC TCTCTCGCGC ACAAAGTTGT
                                                       EagI
                                                     ────
 901  GGAGTCGTTT TTCCTCGGAG CAGGGAAGCG GGCA|GCAGCA GCCGGCCGCG
                                          ───────▶#116 92.2
 951  GGCTTTCTCC CGCCGAGGGG CGAGGAGGAG CCTCTGGCTC CAGAAGCCGA
1001  TTGGGGAATC ACGGGGAGCG GCGCCCCCT TCTTTTGGGT CATTTCTGCA
1051  AACGGAAAAC TCTGTAGCGT TTGGCAAAGT TGGTGCCTGC GCGCCCCTTC
1101  CAGGTTTGCG CTTTGACTGT TTTGTTTTTG GCGGAACTAC CAGGCAGGAA
1151  GATTGCACAA GTAAGGGGCG TTTTCAGTCG GGTGTCAATT TCTCTTTCTT
1201  TCTTTCTTTT TTTAAAATTT CGGTTCGTGT CTGCTTCTCC AAGCTT
                                                  ─────
                                                  HindIII
```

Fig.5A.

```
                       HindIII
  1 ..............AAGCTTGGAACAGGCTCTATAACAGATGTGCGTTTG   36
                  |  |   ||||  ||   ||  ||||     |
751 CACCAGCACCCCAAATACACACAACACACACACACACACACACACACACA  800

37 TGTGTGCATATTGGAAAACAGAAAAA.....TAAGGTCAGCGCAAACACT   81
    || |     | || | ||||        ||||||||||  | ||||||
801 CACACACACACACACACACGGTAAAAATTTTAAAGGTCAGCACCAACACT  850

82 ACTTG....TAATACAAACTAATGTAAGAGAAAACTTCTTTTTCAATATT  127
    | |||    ||  |  |  ||||  |      |  ||  ||   |||
851 ATTTGTGTATATGAACATATAAGGACACTTGGGATTGTTTAGACAGCATT  900

128 AACAACGACACTAGAGAAATAATGTAAAATAAATATACGGTTGGAACTAG  177
    | || ||  | |  ||||  ||||||||||||||||  ||||   |||
901 TAAAATGATCCAAAGAAAATTCCATAAAATAAATATACCCCTGGATTTAG  950

178 GGGTAAAAAAAAAATCAGCAACGTCAGCAAACTGAGATGGGGTGAGTTGG  227
     ||     ||| ||| |||| |||| |||||||  ||||||  || ||||
951 ....AACCCCAAACTCAACAACCTCAGTAAACTGAAATGGGGCGAATTGG  996

228 AAGGCAGATTGGAATTTATCTCTTAACAAAATA...............TC  262
    |  || |||  ||||||  |    |  | ||||                |
997 CCAGAAGGTTGAGATTTATATAAGATAATAATAAAAAAAAAATTAAAGTA 1046

263 ACCCTAACTAGAGACCTGTTTTGCCTAAGGGGACGTGACTCACATTTTCG  312
    | |   ||||||||  |  ||||||   |||||| |  ||||| ||||||||
1047 CTGTTGATAAGAGACCTAGTGTGCCTAGAGGGGTGTGACACACATTTTCG 1096

313 GATAATCTGAATAAGGGGAATTGTGTCTGCTCGAGGCATCCATTCTGGTT  362
    || |||  ||||||||| ||| |||  || ||| | |  ||||| |
1097 GACAATTTGAATAAAGGGCACGGTGCGTGCGCGGTGACTATTCCAG...  1144

363 CGGTCTCCGGACTCCCGGCTCCCGGCACGCACGGTTCACTCTGGAGCGCG  412
    |||    ||  ||  ||  |||||||  ||  |||  | |||| |
1145 ..........CTTCTGGCTTCCAGCACGCACGACTGGTTCCGGGATTCT  1183
                                        ───────
                  AP2                                
413 CGCCCCAGGCCAGCCAAGCGCCGAGCCGGGCTGCTGCGGGCTGGGAGGGC  462
    ||| ||  ||   ||    ||     | ||||||||||||||||||||||
1184 CGCACCGCGCACCGCA.....CGGAGCCGGCTGCTGCGGGCTGGGAGGGC 1228

463 GCGCAGGGCCGGCGCTGATTGACGGGGCGCGCAGTCAGGTGACTTGGGGC  512
    || ||||||  |||||||||||||||||  |||||||||| || ||
1229 GCCTAGGGCTAGCGCTGATTGACCGGGCGCGCGGTCAGGTGACCCGAAGC 1278
                                        E-Box.

513 GCCAAGTTCCCGACGCGGTGGCCGCGGTGACCGCCGAGGCCCGGCAGACG  562
    ||||  |||| |  ||  |  ||||||||  ||||  | |||| ||
1279 GCCACGTTCTGGGAGCCCGGCCCGCGGTGGCTTCCCAGGCCGGGGCAGGA 1328

563 CTGACCCGGGAACGTAGTGGGGCTGATCTTCC.....GGAACAAAGTTGCT  608
    |  ||  || |  ||  |||  ||| |||  ||   |||||||||||||
1329 CCGAACCCGGAGCCGAGGGGGACTGGTCTCCCCGGGAGAACAAAGTTGCC 1378
              SP1
609 GGGCCGGCGGCGGCGGGGCGAGAGCGCCGAGGGGGAGCCGGAGCGCTGCA  658
    ||||  ||||||||||  || |||  ||||||||    || ||
1379 CGGCCTGGGGCCCCGGGCGCGCGAGCGGCGAGACGGCGGGTCCG.....  1423
              AP2·
659 GAGGCGCGGGCCGGAGGGCTGGCGCTGATCTGCACCCTTCTCATCTGGAG  708
     |   |    |||  |||   |   |   |   |
1424 ....................ACCTGCGGGATCCACGGTTCCGAGGTTGGG 1453
              AP2·       AP2·     SmaI ·     Sp1·
709 AGCGGACCCCTGGCTGCCCGGAGGCGAGCCCCTTCCCGGGGGTGGGGGC  758
    |     ||||      || |||||||||||| ||||||||| | |||
1454 TGATTCGTGCTGG.....GAGACGCGAGCCCCTACCCGGGGTGGCGGGCG 1498
                                          SmaI
```

Fig. 5B.

```
 759 GGCAACGCGCGACCCAGCGGTCCTGCGCCCCACCCTCCCTCCTCCGCCTC  808
     | |       | |      | |||||||||||||  |
1499 GACCCAG..............CAGCGCCCCACCCTCGTT..........  1523
                              AP2
 809 CAGCGCTCGGCTCCAACAAAGGGGCAGGCCCGCAGCGG..GGAGGAGGAGG  857
     |||||||||||||||| |||       ||| ||||||   ||
1524 ..........CTCCAACAAAGGGGCCGGCGGAAGCCGGAGGAGGACCTGG  1563

858 AGGAGCCGCCGAAGGAGCGAGCCTCTCTCGCGCACAAAGTTGTGGAGTCG  907
     |||||   ||||  || ||||||  ||||||||||||||||||||||||||
1564 AGGAGGAGCCGGAGCGGCGAGCAGCTCTCGCGCACAAAGTTGTGGAGTCG  1613
              O              #116 92.2   EagI       B2B.
 908 TTTTTCCTCGGAGCAGGGAAGCGGGCAGCAGCAGCCGGCCGCGGGCTTTC  957
     ||||   | ||    |||| ||||||||||      ||||| ||||||  ||||
1614 CCCTTCCCCCGACGAGGGGAGCGGGCAGC....GCCGGGCGCGGGATTTC  1659
          SP1
          SP1
 958 TCCCGCCGAGGGGCGAGGAGGAGCCTCTGGCTCCAGAAGCCGATTGGGGA  1007
     ||||| ||||||||||||||||||  ||||||   |||||||  |||
1660 TCCCGCCCAGGGCCGAGGAGGAGCCCTGGGCTCC.TCAGCCGATCGGGCC  1708

1008 ATCACGGGGAGCGGCGCCCCCCTTCTTTTGGGTCATTTCTGCAAACGGAA  1057
     | | |||||||||||||||||| ||||||  |||||||| ||||| | ||||
1709 ACCTCGGGGAGCGGCGCCCCTTTTCTTTCGGGTCATTCCTGCAGAGGGAA  1758
                 . U25         (A)1088     . PstI
1058 AACTCTGTAGCGTTTGGCAAAGTTGGTGCCTGCGCGCCCCTTCCAGGTTT  1107
     |||||                   |||  ||||||   |   |||||| |
1759 AACTC..................CTGCGTGCGC.CTGCCCCAGGCTA  1787

1108 GCGCTTTGACTGTTTTGTTTTTGGCGGAACTACCAGGCAGGAAGATTGCA  1157
     ||| || |||||||||||||||||||||||||||| |||||||||||||||
1788 GCGTTTGGACTGTTTTGTTTTTGGCGGAACTACCGGGCAGGAAGATTGCA  1837

1158 CAAGT.AAGGGGCGTTTTCAGTCGGGTGTCAATTTCTCTTTCTTTCTTTC  1206
     |||||  ||||||||||| || |||||||||||||    |  |   |
1838 CAAGTCAGGGGGCGTTTCCAATCGGGTGTCAATTTTGGAT..CTCCCCCC  1885
                                     HindIII .
1207 TTTTTTTAAAATTTCGGTTCGTGTCTGCTTCTCCAAGCTTTATTTTTTTT  1256
        || || |||| |  | |||||| ||| ||      ||
1886 CCCCAACCCCCCTTTGGATCTTGTCGGGCTTTCCACGTTTCA....CTTA  1931
                                 . Primer BFB .
1257 TTAAAATACATCGCACCACCAAACTAACACTCGCACACACCCCCGCGGTT  1306
     ||||   |  | |  | ||  |   |||  |||||
1932 AAAAAAATTCTTGTAACGTCCAAGGCAAGCTCCCCACCACCC........  1973

1307 ACTCCGTGTCAAACTCCTAGAGGAGCCCTTGGCCAGCTCGGGGTGCGGCG  1356
       | ||| || |||||| || | ||| ||
1974 ........GAACACGCCCAGAGGAACCTTGGGGCCTCT............  2003
                                      Exon1
1357 GTGGCGACCGGCAGGCGAGGAGGCCCGCGGGCAGCAGGTAAGCCCATGCA  1406
     ||  |   ||  |||||||||||||||||||||||||||
2004 .................GGGACTTGGCTAGCAGGTAAGCCCATGCA  2032

1407 TTATTGAAGCCTCGGGCT.GGTAATGTGACTACAGCCCCCGAGGGAATGG  1455
     |||||||||| ||||| |||||||||||| ||| |||| ||||||||
2033 TTATTGAAGCTTCGGTCTGGGTAATGTGACCGCAGTCCCCTAGGGAATGG  2082
         SP1
1456 GGCGGGGGCCGGGAGGAGGATGGCTCTTTCTGCGGTTCTTCCGCCTGGGA  1505
     ||||||||  |  |||||| || |||||||| |||| ||||| |||
2083 GGCGGGGGTTGAAAGGAGGTGGGACCTTTCTGCAGTTCCACCGCCCGGGT  2132
                                                Smal .
1506 TCGGCGTCCCGAGCTGCTTCCCAAGTCCCAGAGTCGAAGATGGGAGTAAC  1555
      ||   |      |     ||||||  ||    ||     | ||
2133 CCCG....AAGTAGCTGTAGCCAACTTCTGCACTTTCCCTGGAAGCTCAG  2178
```

Fig.5C.

```
            AP1
1556 TTTTGCGTGCCCTTTCCTCGGGGCCTCAGTTTAGCTCCCCGCGGTGCGAG 1605
     |  | ||||    |   || |    |||       | |     |
2179 CGTCCCCTGCCTGGGCGGGAGAGAGCTGGGTTGAGAAGGTGGGAATCTGT 2228
                                              BamHI.
1606 AGAGAATGCCGGAGGCGTGGAGAGCTCGGGCGTGGAGGTCCTTGGGATCC 1655
     |  |  |||   | |  ||   || || |  |       ||    |
2229 ACTGGTCGCCACGGTCTCAGATTCCTAGGTCTAGTTTAGTACTGTTGTTT 2278
```

UTROPHIN GENE PROMOTOR

The present invention is based on cloning of a genomic promoter region of the human utrophin gene and of the mouse utrophin gene.

The severe muscle wasting disorders Duchenne muscular dystrophy (DMD) and the less debilitating Becker muscular dystrophy (BMD) are due to mutations in the dystrophin gene resulting in a lack of dystrophin or abnormal expression of truncated forms of dystrophin, respectively. Dystrophin is a large cytoskeletal protein (427 kDa with a length of 125 nm) which in muscle is located at the cytoplasmic surface of the sarcolemma, the neuromuscular junction (NMJ) and myotendinous junction (MTJ). It binds to a complex of proteins and glycoproteins spanning the sarcolemma called the dystrophin associated glycoprotein complex (DGC). The breakdown of the integrity of this complex due to loss of, or impairment of dystrophin function, leads to muscle degeneration and the DMD phenotype.

The dystrophin gene is the largest gene so far identified in man, covering over 2.7 megabases and containing 79 exons. The corresponding 14 kb dystrophin mRNA is expressed predominantly in skeletal, cardiac and smooth muscle with lower levels in brain. Transcription of dystrophin in different tissues is regulated from either the brain promoter (predominantly active in neuronal cells) or muscle promoter (differentiated myogenic cells, and primary glial cells) giving rise to differing first exons. A third promoter between the muscle promoter and the second exon of dystrophin regulates expression in cerebellar Purkinje neurons. Recently reviewed in [1,2,3].

There are various approaches which have been adopted for the gene therapy of DMD, using the mdx mouse as a model system. However, there are considerable problems related to the number of muscle cells that can be made dystrophin positive, the levels of expression of the gene and the duration of expression [4]. It has also become apparent that simply re-introducing genes expressing the dystrophin carboxy-terminus has no effect on the dystrophic phenotype although the DGC appears to be re-established at the sarcolemma [5,6].

In order to circumvent some of these problems, possibilities of compensating for dystrophin loss using a related protein, utrophin, are being explored as an alternative route to dystrophin gene therapy. A similar strategy is currently being evaluated in clinical trials to upregulate foetal haemoglobin to compensate for the affected adult-globin chains in patients with sickle cell anaemia [7,8].

Utrophin is a 395 kDa protein encoded by multiexonic 1Mb UTRN gene located on chromosome 6q24 [9]. At present the tissue regulation of utrophin is not fully understood. Unlike dystrophin, only one promoter has so far been detected. In the dystrophin deficient mdx mouse, utrophin levels in muscle remain elevated soon after birth compared with normal mice; once the utrophin levels have decreased to the adult levels (about 1 week after birth), the first signs of muscle fibre necrosis are detected. However there is evidence to suggest that in the small calibre muscles, continual increased levels of utrophin can interact with the DGC complex (or an antigenically related complex) at the sarcolemma thus preventing loss of the complex with the result that these muscles appear normal. There is also a substantial body of evidence demonstrating that utrophin is capable of localising to the sarcolemma in normal muscle. During fetal muscle development there is increased utrophin expression, localised to the sarcolemma, up until 18 weeks in the human and 20 days gestation in the mouse. After this time the utrophin sarcolemmal staining steadily decreases to the significantly lower adult levels shortly before birth where utrophin is localised almost exclusively to the NMJ. The decrease in utrophin expression coincides with increased expression of dystrophin. See reviews [1,2,3].

Thus, in certain circumstances utrophin can localise to the sarcolemma probably at the same binding sites as dystrophin, through interactions with actin and the DGC. Accordingly, if expression of utrophin is sufficiently elevated, it may maintain the DGC and thus alleviate muscle degeneration in DMD/BMD patients [11].

However, manipulation of utrophin expression and screening for molecules able to upregulate expression is hampered by the utrophin promoter not having been cloned. Though a cDNA encoding sequence for utrophin is available, the sequence-of the upstream untranslated region is not and, given the large number of introns in the utrophin gene [9], it is not surprising that there has been no reported successful identification and isolation of the utrophin promoter.

We have now cloned a utrophin promoter and the present invention in various aspects and embodiments is based on the sequence information obtained and provided herein.

One major use of the promoter is in screening for substances able to modulate its activity. It is well known that pharmaceutical research leading to the identification of a new drug generally involves the screening of very large numbers of candidate substances, both before and even after a lead compound has been found. This is one factor which makes pharmaceutical research very expensive and time-consuming. A method or means assisting in the screening process will have considerable commercial importance and utility. Substances identified as upregulators of the utrophin promoter represent an advance in the fight against muscular dystrophy since they provide basis for design and investigation of therapeutics for in vivo use.

According to a first aspect, the present invention provides a nucleic acid isolate comprising a utrophin gene promoter.

In a second aspect, the present invention provides a nucleic acid isolate comprising a promoter, the promoter comprising a sequence of nucleotides shown in FIG. 2 or FIG 5. The promoter may comprise one or more fragments of the sequence shown in FIG. 2 or FIG. 5, sufficient to promote gene expression. The promoter may comprise or consist essentially of a sequence of nucleotides 5' to position 898 in FIG. 2 or FIG. 5, for the human, or an equivalent sequence in the mouse. Preferably such a promoter comprises or consists essentially of nucleotides numbered 746–944 in the sequence shown in FIG. 2 or the human sequence of FIG. 5, or the equivalent mouse sequence of FIG. 5. An even smaller portion of this part of the sequence of FIG. 2 or FIG. 5 may be used as long as promoter activity is retained. Restriction enzyme or nucleases may be used to digest the nucleic acid, followed by an appropriate assay (for example as illustrated herein using luciferase constructs) to determine the minimal sequence required. A preferred embodiment of the present invention provides a nucleic acid isolate with the minimal nucleotide sequence shown in FIG. 2 or FIG. 5 required for promoter activity. The minimal promoter element is situated between the SmaI and EagI restriction sites located at 746 and 942 bp respectively in the human sequence and 1486 and 1645 bp respectively in the mouse sequence (see FIG. 5).

The promoter may comprise one or more sequence motifs or elements conferring developmental and/or tissue-specific regulatory control of expression. For instance, the promoter may comprise a sequence for muscle-specific expression, e.g. an E-box element/myoD binding site, such as CANNTG, preferably CAGGTG. This may be upstream (5') of a promoter sequence as discussed above, e.g. at nucleotides 498–503 using the numbering of FIG. 2. The promoter may comprise a sequence for synaptic expression, e.g. TTCCGG, which may be upstream (5') of a promoter sequence as discussed above, e.g. at nucleotides 591–596 using the numbering of FIG. 2. Other regulatory sequences may be included, for instance as identified by mutation or digest assay in an appropriate expression system or by sequence comparison with available information, e.g. using a computer to search on-line databases.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The present invention extends to a promoter which has a nucleotide sequence which is allele, mutant, variant or derivative, by way of nucleotide addition, insertion, substitution or deletion of a promoter sequence as provided herein. Systematic or random mutagenesis of nucleic acid to make an alteration to the nucleotide sequence may be performed using any technique known to those skilled in the art. One or more alterations to a promoter sequence according to the present invention may increase or decrease promoter activity, or increase or decrease the magnitude of the effect of a substance able to modulate the promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene-as discussed further below facilitates determination of promoter activity by reference to protein production.

In various embodiments of the present invention a promoter which has a sequence that is a fragment, mutant, allele, derivative or variant, by way of addition, insertion, deletion or substitution of one or more nucleotides, of the sequence of the promoter shown in FIG. 2 or the mouse promoter shown in FIG. 5, has at least about 60% homology with one or both of the shown sequences, preferably at least about 70% homology, more preferably at least about 80% homology, more preferably at least about 90% homology, more preferably at least about 95% homology. The sequence in accordance with an embodiment of the invention may hybridise with one or both of the shown sequences, or the complementary sequences (since DNA is generally double-stranded). The sequence may have the ability to promote transcription (i.e. have "promoter activity") in muscle cells, e.g. human muscle cells, or muscle-specific transcription.

Further provided by the present invention is a nucleic acid construct comprising a utrophin promoter region or a fragment, mutant, allele, derivative or variant thereof able to promoter transcription, operably linked to a heterologous gene, e.g. a coding sequence. By "heterologous" is meant a gene other than utrophin. Modified forms of utrophin are generally excluded. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Expression of a reporter gene from the promoter may be in an in vitro expression.system or may be intracellular (in vivo). Expression generally requires the presence, in addition to the promoter which initiates transcription, a translational initiation region and transcriptional and translational termination regions. One or more introns may be present in the gene, along with mRNA processing signals (e.g. splice sites).

Systems for cloning and expression of a polypeptide in a variety of different host cells are well known. Suitable host cells generally include bacteria, mammalian cells, yeast and baculovirus systems. Mammalian cells are preferred for use in the present invention. Mammalian cell lines available in the art for expression of a heterologous polypeptide include Chinese hamster ovary cells, HeLa cells, baby hamster kidney cells, human glioma cells, and many others, including other human cell lines. A common, preferred bacterial host is *E. coli*.

The present invention also provides a nucleic acid vector comprising a promoter as disclosed herein. Such a vector may comprise a suitably positioned restriction site or other means for insertion into the vector of a sequence heterologous to the promoter to be operably linked thereto.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Procedures for introducing DNA into cells depend on the host used, but are well known.

Thus, a further aspect of the present invention provides a host cell containing a nucleic acid construct comprising a promoter element, as disclosed herein, operably linked to a heterologous gene. A still further aspect provides a method comprising introducing such a construct into a host cell. The introduction may employ any available technique, including, for eukaryotic cells, calcium phosphate transfection, DEAE-Dextran transfection, electroporation, liposome-mediated transfection and transduction using retrovirus.

The introduction may be followed by causing or allowing expression of the heterologous gene under the control of the promoter, e.g. by culturing host cells under conditions for expression of the gene.

In one embodiment, the construct comprising promoter and gene is integrated into the genome (e.g. chromosome) of the host cell. Integration may be promoted by inclusion in the construct of sequences which promote recombination with the genome, in accordance with standard techniques.

Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992, the disclosure of which is incorporated herein by reference.

Nucleic acid molecules, constructs and vectors according to the present invention may be provided isolated and/or purified (i.e. from their natural environment), in substantially pure or homogeneous form, free or substantially free of a utrophin coding sequence, or free or substantially free of nucleic acid or genes of the species of interest or origin other than the promoter sequence. Nucleic acid according to the present invention may be wholly or partially synthetic. The term "isolate" encompasses all these possibilities.

Nucleic acid constructs comprising a promoter (as disclosed herein) and a heterologous gene (reporter) may be employed in screening for a substance able to modulate activity of the promoter. For therapeutic purposes, e.g. for treatment of muscular dystrophy, a substance able to up-regulate expression of the promoter may be sought. A method of screening for ability of a substance to modulate activity of a utrophin promoter may comprise contacting an expression system, such as a host cell, containing a nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the utrophin promoter.

A promoter construct may be transfected into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed. Previous experiments testing the effects of glucocorticoids on the endogenous utrophin protein and RNA levels in myoblasts have already been described [12,13] and techniques used for those experiments may similarly be employed.

Constructs comprising one or more developmental and/or time-specific regulatory motifs (as discussed) may be used to screen for a substance able to modulate the corresponding aspect of the promoter activity, e.g. muscle and/or synapse-specific expression.

Following identification of a substance which modulates or affects utrophin promoter activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of utrophin promoter activity, in accordance with what is disclosed herein, but also a pharmaceutical composition, medicament, drug or other composition comprising such a substance, a method comprising administration of such a composition to a patient, e.g. for increasing utrophin expression for instance in treatment of muscular dystrophy, use of such a substance in manufacture of a composition for administration, e.g. for increasing utrophin expression for instance in treatment of muscular dystrophy, and a method of making a pharmaceutical composition comprising admixing such a substance with a pharmaceutically acceptable excipient, vehicle or carrier, and optionally other ingredients.

Administration will preferably be in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the-active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Instead of a substance identified using a promoter as disclosed herein, a mimetic or mimick or the substance may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process. In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate utrophin promoter activity using a screening method as disclosed herein are included within the scope of the present invention.

Modifications to and further aspects and embodiments of the present invention will be apparent to those skilled in the art. All documents mentioned herein are incorporated by reference.

Experimental basis for and embodiments of the present invention will now be described in more detail, by way of example and not limitation, and with reference to the following figures:

BRIEF DESCRIPTION OF THE DRAWINGS

FIG. 2 shows the nucleic acid sequence of a 1246 bp HindIII fragment which comprises a human utrophin promoter and first utrophin gene exon, including restriction endonuclease sites which may be used to derive reporter constructs, and putative transcription factor binding sites. (SEQ ID NO: 1.)

FIGS. 5A–5C show sequence and phylogenetic conservation of a promoter region of utrophin and untranslated exon 1. The human sequence is printed above and the mouse sequence below. The location of the major transcription initiation sites in human by primer extension assays and 5' RACE analysis are respectively indicated by closed ▼ triangles and open triangles ▽. The major cap site found for mouse by RNase protection is indicated by an open circle ○. Putative regulatory motifs are boxed. The primers A and B used for RT PCR in the mouse are indicated, and the splice junction for exon 1—intron 1 is marked. (SEQ ID NO: 2 and SEQ ID NO: 3)

Isolation of a utrophin promoter

Figure 1:
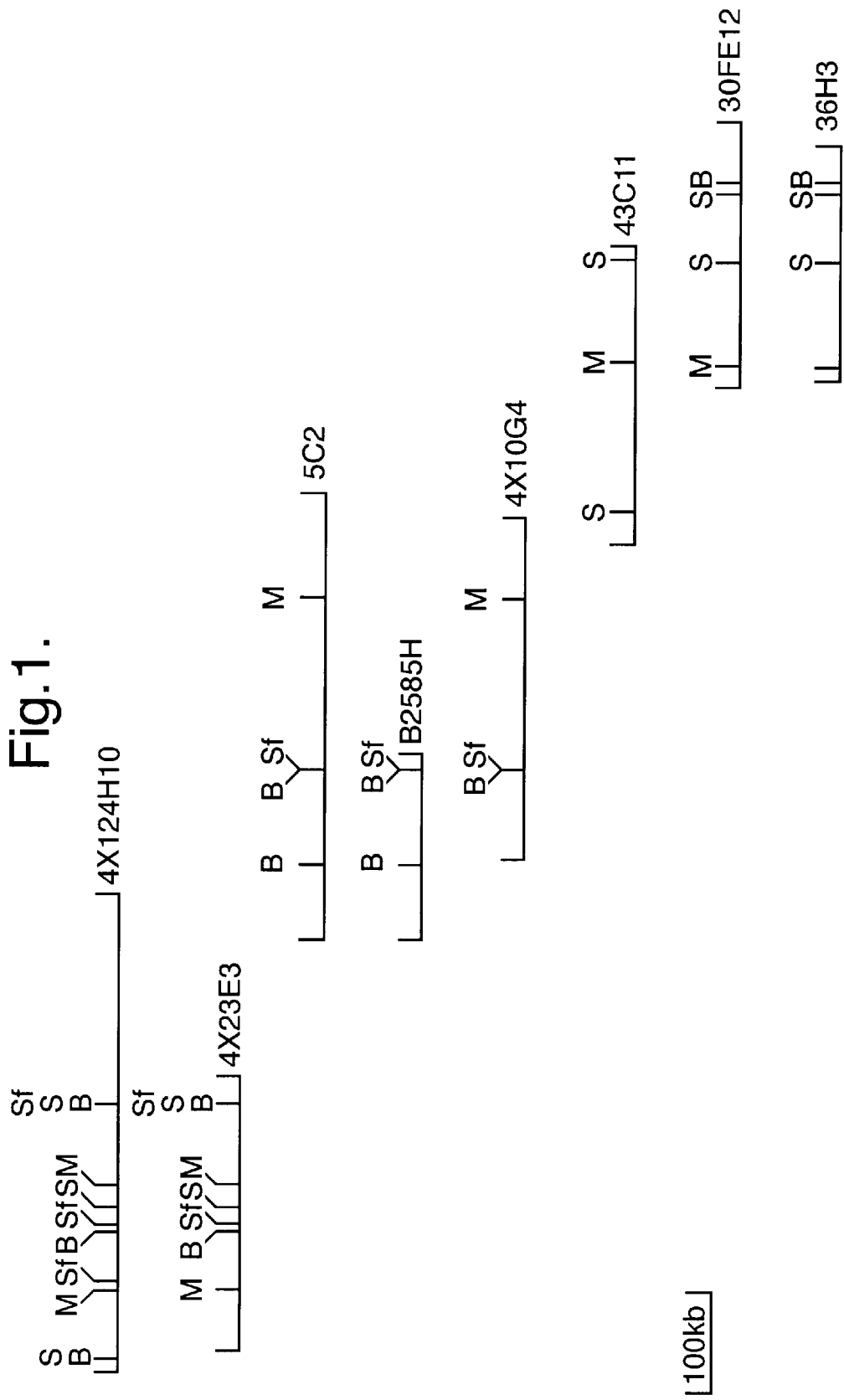
FIG. 1 shows overlapping yeast artificial chromosomes (YACs) covering the complete genomic region of human utrophin.

The complete genomic region of human utrophin was cloned in a series of overlapping yeast artificial chromosomes (YACs) as shown in FIG. 1. YAC 4X23E3(YAC23) was shown to contain only human utrophin exons 1 and 2 as well as containing a cluster of rare cutting enzymes. The corresponding genomic region was shown to be unmethylated [9]. Considering these results, YAC23 was thought to contain a utrophin promoter.

YAC23 was randomly subcloned into λGEM-11 to generated a library. After screening with a 350 bp SacII fragment containing the most 5' sequences of the utrophin cDNA, a number of positive hybridising phage were further subcloned into pUC18 plasmid. One of these subclones, 1246 bp HindIII fragment was sequenced and shown to contain the putative utrophin promoter and first exon. FIG. 2 shows this sequence and includes putative transcription factor binding sites.

Reporter Gene Expression

In order to identify the promoter element of utrophin, a series of reporter constructs containing different regions of the 5' UTR of the utrophin gene were assayed for transcriptional activity.

Fire-fly luciferase was used as a reporter gene and plasmids were constructed by cloning different fragments of the 5' UTR of the utrophin gene into a polylinker site 5' of the cDNA coding for the firefly luciferase in the pGL2-Basic vector (Promega). Human cell line (IN157) cells were transfected with 50 $\mu$g of test plasmid and 10 $\mu$g of an internal control plasmid pSV-β-gal (Promega) which contains the β-galactosidase gene driven by the SV40 promoter. Transfection was performed by electroporation of $3 \times 10^6$ cells, 0.8 ml volume of 0.4 $cm^2$ cuvettes, at 0.25 V and capacitance of 960 $\mu$F. Cells were allowed to recover on ice for 1 minute before being plated into 4 mls of growth media. Cells were harvested at 24 hours after transfection and were lysed in 400 $\mu$l of 1x Reagent Lysis Buffer (Promega).

The luciferase activity assay was initiated by mixing 20 $\mu$l of cell lysate with 100 $\mu$l of luciferase assay reagent (Promega) and the light emitted was integrated over a 10 second interval on a luminometer (Turner design), and expressed as light units. β-galactosidase activity was assayed using 50 $\mu$l of the same cell lysate mixed with an equal volume of 2× Assay Reagent (Promega), incubated 37° C. for 3 hours and the absorbance at 420 nm measured using a spectrophotometer. The luciferase activity was normalised to the β-galactosidase activity derived from the cotransfected internal control plasmid to correct for differences in transfection efficiency.

Figure 3:
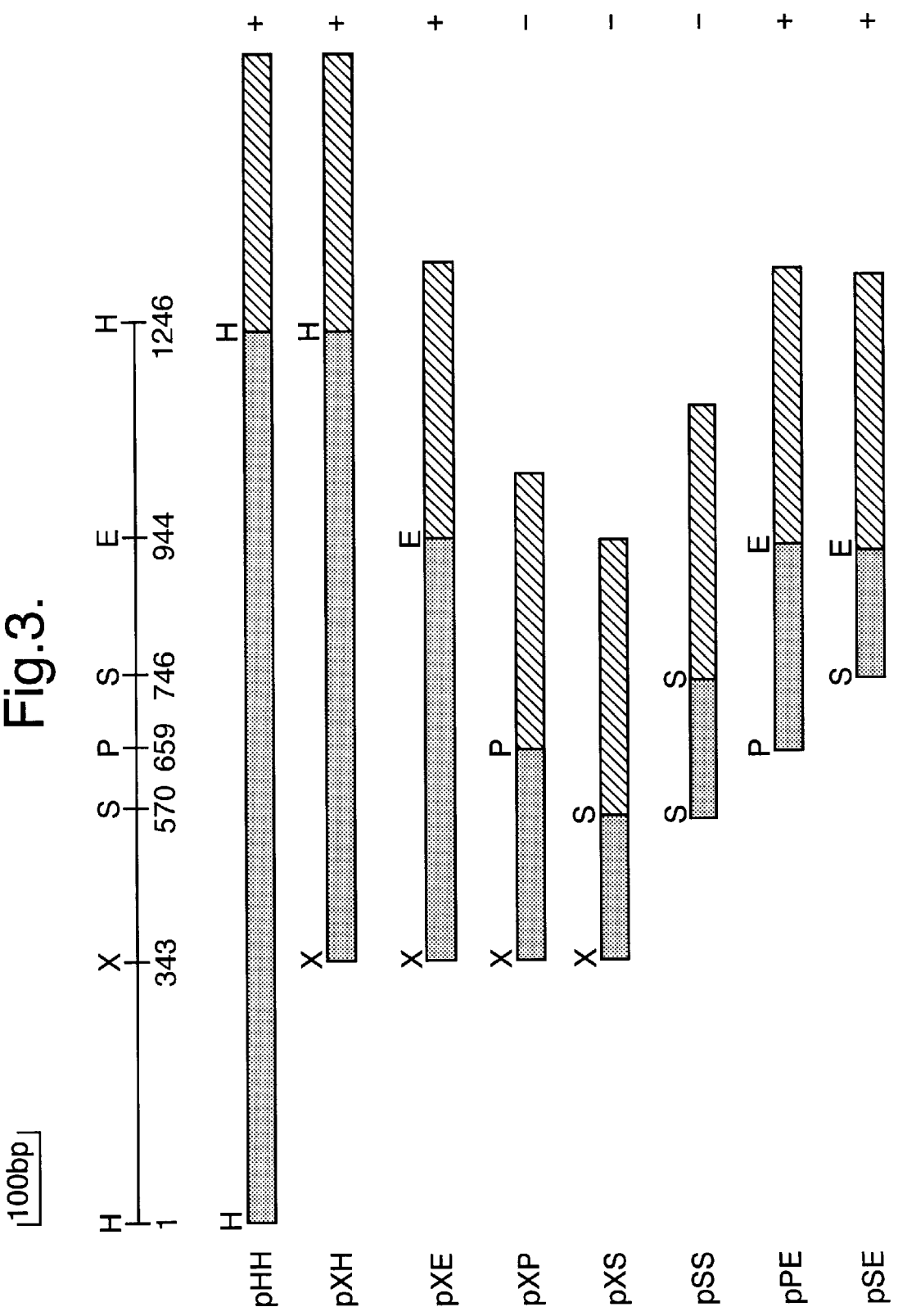
FIG. 3 shows a restriction endonuclease map of the 1246 bp HindIII fragment of FIG. 2, and various constructs used in the functional assay of the utrophin promoter, each construct comprising a luciferase gene (denoted by the hatched bar) operably linked to a different fragment of the 1246 bp region. H=HindIII; X=XhoI; S=SmaI, P=PstI; E=EagI "+" and "=" refer to luciferase activity.
Figure 4:
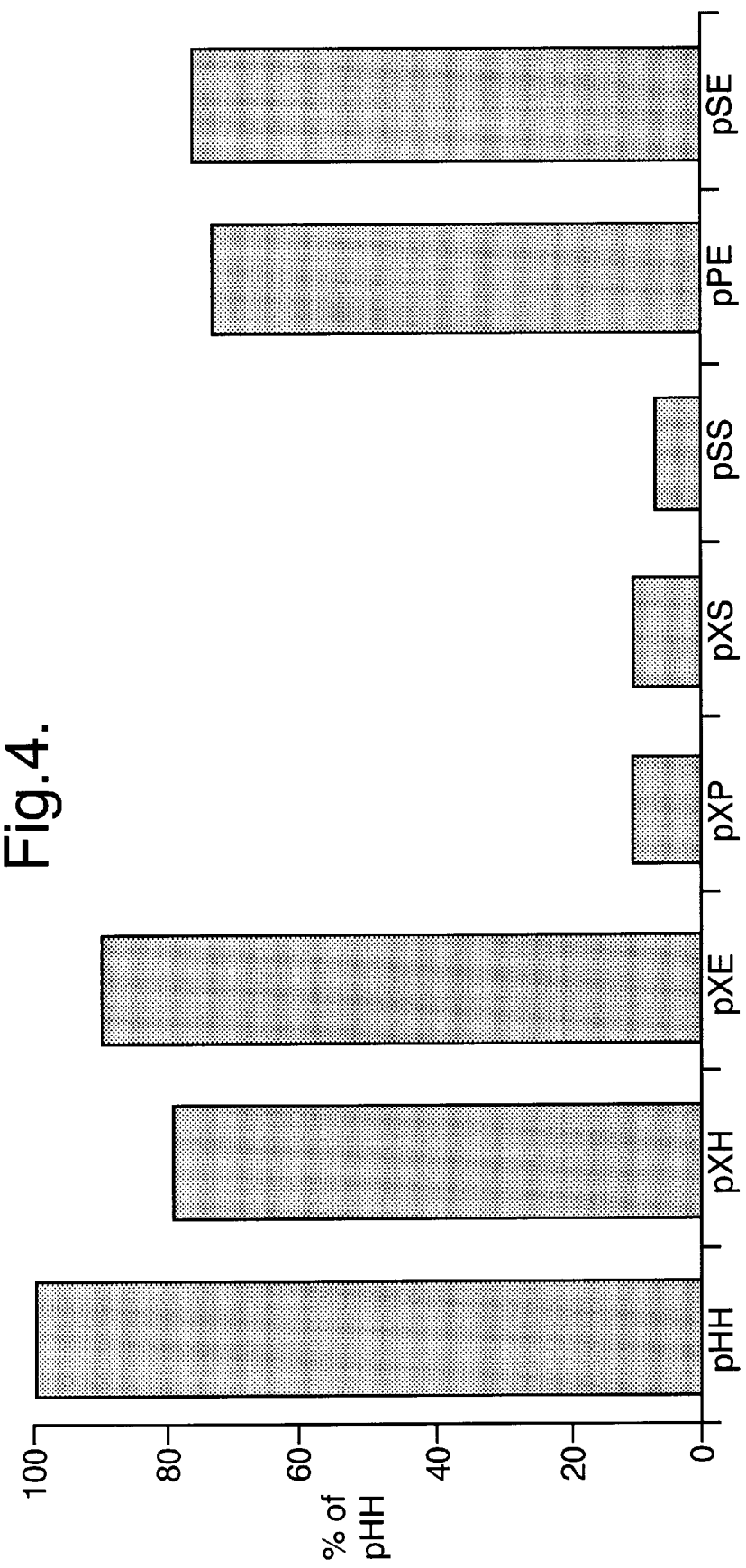
FIG. 4 shows normalised luciferase activity resulting from transcription of the utrophin promoter constructs shown in FIG. 3, expressed as the percentage of the activity of the pHH construct. The histogram shows the mean of the results from transfection experiments.

FIG. 3 illustrates the different constructs used in the functional assay of the utrophin promoter. In FIG. 4 the normalised luciferase activity resulting from transcription of the utrophin promoter constructs is expressed as the percentage of the activity of the pUPB-LUC construct. The histogram shows the mean of the results from three transfection experiments each of which was performed in triplicate.

Several constructs display transcriptional activity as a result of the presence of the utrophin promter. Comparison of the activity between the constructs demonstrates that the minimal promoter element lies with the 200 bp PstI-EagI fragment (FIG. 4).

Deletions of other regions within the 5' flanking sequence, including the conserved E-box (nucleotides 498–503) and TTCCGG motif (nucleotides 591–596), do not affect appreciably the activity of the utrophin promoter in IN157 cells. However, this could be explained by the absence of appropriate transcriptional factors within the IN157 cells that may be capable of interacting with the DNA motifs.

Analysis of the promoter region

To delineate DNA elements that may regulate the activity of the utrophin gene promoter, the equivalent mouse promoter was isolated. A mouse genomic phage library was screened with the human 0.6 kb probe. Positive phage were further subcloned into plasmid and a 2.2 kb EcoRl subclone (M2.2) was sequenced. FIG. 5 shows an alignment between the two corresponding sequences, displaying limited overall conservation across exon 1 of human and mouse, which may reflect the lower evolutionary constraints of non-coding sequence. The consensus splice site for exon 1 is conserved between human and mouse genomic sequence.

The sequence of the first exon and 5' flanking sequence has a very high GC content. Database searches of the human utrophin promoter sequence revealed 99% identity to an uncharacterised GC-rich sequence, identified as a CpG island according to the method described by Cross et al. (14). This sequence corresponds to position 988–1212 (FIGS. 5A–5C) which is in exon 1 of the human utrophin gene and correlates to our previous findings that the 5' UTR of utrophin is unmethylated (9).

Sequence analysis reveals the absence of TATA and CAAT motifs common to eukaryotic promoters, and the presence of several potential binding sites for the transcription factor Sp1. However, the Sp1 binding sites are not conserved between human and mouse and may indicate that these sites are not involved in the transcriptional regulation of utrophin or that there is no constraint for the position to be conserved between species.

A consensus E-box element (CANNTG), involved in regulating muscle gene expression (17), is conserved between both species (FIGS. 5A–5C). A recently identified DNA element (TTCCGG) which appears to regulate synaptic expression of the mouse acetylcholine receptor δ-subunit is present in the 5' flanking sequence of both the human and mouse utrophin gene, although in different positions (FIGS. 5A–5C).

Identification of the putative transcription start site

Different levels of utrophin expression were observed in human cell lines by RNase protection using a probe derived from the carboxy terminus. Utrophin was shown to be expressed at differing levels in the cervical cancer Hela cell line, adult kidney CL11T47 cell line, adult myoblast primary culture and rhabdomyosarcoma IN157 cell line, with the highest levels in IN157 and CL11T47. IN157 was the cell line used in the following assays to identify the start of human transcript.

Primer Extension

A 22-mer oligonucleotide (U25) with its 5' end starting at nucleotide 1088 in exon 1 of the human utrophin gene was used for primer extension assays with RNA isolated from Hela cells, CL11T47 kidney cells and rhabdomyosarcoma IN157 cells. The sizes of the bands generated by extension were 190 bp and 138 bp, which correspond to transcription initiation at nucleotides 898 and 950 respectively on the human sequence (FIGS. 5A–5C). The larger band extends the start of transcription 37 bp upstream from the 5' end of the most 5' utrophin cDNA isolated. The larger product, representing an initiation site at nucleotide 898, was observed in all the cell lines analysed. However the smaller product was generated only in IN157 rhabdomyosarcoma cells and CL11T47 kidney cells.

5' Race

In order to characterise the 5' end of the human transcript, the oligonucleotide U25, described for primer extension above, was used for cDNA synthesis and PCR amplification of RNA from the IN157 rhabdomyosarcoma cell line. The amplified products were subcloned and hybridised with the 0.6 kb cDNA fragment containing the 5' end of utrophin. Sequence analysis of the positive clones indicated a putative start site at position 907 on the human sequence (FIGS. 5A–5C). This is 9 bp downstream from the start site predicted from the major band generated in the primer extension assays. A 20-mer oligonucleotide (U71) with its 5' end corresponding to 170 bp downstream from the start of exon 2 (within the untranslated region) was also used for RACE analysis with RNA from IN157 cells. The sequence of positive hybridising subcloned products predicted a putative initiation site at nucleotide 1214. This may represent a more 3' transcription start site, although it does not correlate to the smaller product identified in the primer extension assays.

The most 5' site for transcription initiation of the human utrophin transcript predicts a putative cap site at nucleotide 898 bp, which is 587 bp upstream from the translation initiation codon, and estimates the size of exon 1 as 495 bp. The identification of additional putative starts of transcription may represent multiple clustered cap sites for the utrophin transcript. The major transcription start sites of the utrophin mRNA lie between positions 898 to 916 of the human sequence (FIGS. 5A–5C) or positions 1604 to 1622 of the mouse sequence.

RNase Protection

Probably because of the very high GC content, we experienced technical difficulties in applying RNase protection analysis across the 5' UTR of human utrophin, a problem also described in the analysis of the GC-rich promoter of the human Dp71dystrophin isoform (16). In order to try to circumvent this problem we used the mouse transcript, which is less GC rich, for RNase protection assays. A complementary RNA probe was synthesised encompassing the SmaI-PstI fragment from positions 743–1051 (FIGS. 5A–5C), which spans the putative cap site of the human transcript. Using an RNA probe complementary to sequence within the carboxy-terminal domain .as a control for utrophin expression, we were able to demonstrate that the utrophin transcript was present at abundant levels in mouse lung, however using the SmaI-PstI RNA probe at hybridisation temperatures of 42° C. and 50° C. we were unable to detect a protected product. A major band of approximately 130 bp only started to appear at a hybridisation temperature of 55° C. and increased in intensity with increasing hybridisation temperatures. The protected fragment observed was reproducibly a broad band suggesting that the start of transcription may vary over several nucleotides.

To demonstrate that this 130 bp product was specific to utrophin, the SmaI-PstI RNA probe was hybridised to RNA from mouse lung and liver and the protected fragment was detected at similar levels as observed using the carboxyterminal probe. No protected product was detected when hybridising the mouse SmaI-PstI probe to RNA isolated from human rhabdomyosarcoma IN157 cells, indicating that the probe is specific to the mouse transcript. This protected band of approximately 130 bp predicts the start of transcription to lie at approximately nucleotide 916 on the human sequence, which is 9 bp and 18 bp downstream from the most 5' cap site predicted by RACE and primer extension assays respectively for the human transcript (FIGS. 5A–5C). These findings suggest that a similar site for transcription initiation is utilised in human and mouse. It should be noted that the region of sequence encompassing the most 5' putative cap sites is highly conserved between the two species.

RT-PCT

In dystrophin, the 5' promoters regulate the tissue-specific expression of full-length isoforms, all of which have a unique first exon spliced to a common second exon. To test the extent the putative utrophin promoter utilises the first untranslated exon, RNA from mouse brain, skeletal muscle, small intestine, liver, lung, spleen, heart, kidney and eye were used as templates for cDNA synthesis and PCR amplification.

Primers were designed to amplify a region across exon 1 and exon 2 thus eliminating the risk of false positives due to contamination by genomic DNA. Amplification using a forward primer (BFB) and reverse primer (U71) with 5' ends complementary to position 1230 in exon 1 and 172 bp downstream of the start of exon 2, respectively, generated an expected product of 283 bp. A second pair of primers with 5' ends at position 894 in exon 1 (B2A) and 153 bp from the start of exon 2 (U73) amplified the expected product of 575 bp. These expected products were observed in all mouse tissues tested. This suggests that the utrophin promoter described here is active in driving the expression of a transcript containing the untranslated first exon and the second exon, which has the translation initiation ATG, in all tissues tested.

In addition, amplification with the primer starting at nucleotide 894 indicates that the mouse transcript extends as far upstream as that predicted from the human transcript. This extends the start site for the mouse transcript approximately 20 bp upstream of that predicted from RNase protection assays and this may represent multiple 5' start sites for the mouse utrophin transcript, as observed for the human transcript. A comparatively lower level of amplification was observed for the more 5' forward primer (B2A), which lies near the putative start of transcription, compared to primer (BFB) starting further downstream in exon 1. It is possible that this upstream primer is complementary to a region spanning the cap site and therefore the primer may only partially anneal to the 5' end of transcript and result in the weak amplification observed for several PCR conditions. In support of this proposition, primers complementary to sequences further upstream than position 894 were unable to generate a product using a range of PCR conditions, indicating that there are no additional upstream cap sites.

DISCUSSION

Utrophin has a CpG island, in contrast to the muscle and brain promoters of the dystrophin gene which have no CpG island. We have isolated and characterised a CpG-rich genomic fragment which contains the first exon and 5' flanking sequence of utrophin. The fragment is active in initiating transcription of a reporter gene in various cell lines, indicating that the utrophin promoter element may be conserved. A series of 5'-deleted fragments of the utrophin upstream flanking region were generated to determine the minimal promoter element. Provided the 155 bp region containing the promoter element was intact, 5' deletions did not significantly alter the transcriptional activity in human rhabdomyosarcoma IN157 cells. Hence, the CpG-rich 155 bp region characterised here may function as a basal promoter element, driving utrophin transcription in many cell types, and it may be the presence of specific transcription factors that regulate the level of utrophin expression. Future investigation into the transcriptional activity of these constructs in different cellular backgrounds, may reveal the regulatory DNA elements controlling utrophin expression.

The utrophin promoter region has several putative Sp1 binding sites and is devoid of TATA or CAAT motifs. By primer extension, 5' RACE and RNase protection analysis, we have located several putative cap sites for the full-length utrophin transcript. Although we cannot rule out the possibility that these additional products arose due to premature termination by reverse transcriptase during primer extension and RACE analysis, these results would be consistent with the observation that CpG-rich TATA-less promoters of widely expressed genes usually contain several transcription initiation sites spread over a fairly large region, rather than at a single base position (9).

Genes with CpG-rich promoters were initially considered to express proteins with a housekeeping function in the cell. However, several genes devoid of TATA or CAAT motifs in their promoter regions have been shown to encode proteins that are highly regulated (17,22). Expression of the acetylcholinesterase gene, which also has a CpG-rich promoter, is regulated during muscle cell differentiation and is localised specifically at the NMJ (18). The typical "house-keeping" promoter of the Dp71dystrophin isoform drives expression in specific cell types (16). Utrophin, although expressed in all tissues, also appears to be regulated in different cell types, for example there are relatively abundant levels in adult lung and higher levels in foetal muscle compared to adult skeletal muscle (19). We have shown here that the utrophin transcript is detected at different levels in various human cell lines. Utrophin transcripts are also specifically localised during development, with initial accumulation in the neural tube and later becoming abundant at a variety of other sites such as the tendon primordia in the digits, the pituitary thyroid and adrenal glands, cardiac muscle, and the kidney and lung (20). Taken together, these observations suggest that, although utrophin is expressed widely, there is also developmental- and tissue-specific regulation of expression in certain tissues.

Several putative DNA motifs identified in the 5' flanking sequence may be involved in the control of utrophin muscle expression. We identified a conserved E-box, which is a binding site for helix-loop-helix proteins of the MyoD1 family, including MyoD1 myogenin, MRF4 and myf5. E-box motifs are found in the promoters of many muscle-specific genes, including the a, b and g acetylcholine receptor subunit genes. Given the co-localisation of utrophin with acetylcholine receptors at the NMJ, it would be of interest to determine whether myogenic factors regulate the expression of utrophin by interaction with this conserved E-box motif. The human and mouse utrophin 5' flanking region contain the core sequence of the N box, an element shown to direct synapse-specific expression of the mouse acetylcholine receptor δ-subunit gene (15). This TTCCGG motif restricts the expression of the d-subunit gene to the NMJ by enhancing expression at the endplate and acting as a silencer in extrajunctional areas. Sequences identical to this core sequence of the N box are present in other AChR subunit genes and it is likely that this element regulates the synaptic expression of at least some of these genes (16). The mRNA levels of N-CAM, 43 K-rapsyn and s-laminin (21) were shown by in situ hybridisation to be concentrated at the synaptic sites. By sequence analysis, we have determined that the core sequence of the N box is present in the 5' flanking of b2-syntrophin, which is also localised specifically to the NMJ, however it is absent from the upstream sequence of al-syntrophin, which is expressed throughout the general sarcolemma. This suggests that there may be a general mechanism for selective transcription by synaptic nuclei and this may involve the interaction of a transcription factor(s) capable of recognising the N box sequence.

References

1. Tinsley, et al. (1994) *Proc Natl Acad Sci.* USA 91: 8307–8313.
2. Blake, et al. (1994) *Trends in Cell Biol.* 4: 19–23.
3. Tinsley, et al. (1993) *Curr Opin Genet Dev.* 3: 484–90.
4. Partridge, et al. (1995) *British Medical Bulletin* 51: 123–137.
5. Cox, et al. (1994) *Nature Genet* 8: 333–339.
6. Greenberg, et al. (1994) *Nature Genet* 8: 340–344.
7. Rodgers, et al. (1993) *N Engl J Med.* 328: 73–80.
8. Perrine, et al. (1993) *N Engl J Med.* 328: 81–86.
9. Pearce, et al. (1993) *Hum Mol Gen.* 2: 1765–1772.
10. Winder, et al. (1995) *J. Cell Sci.* 108: 63–71.
11. Tinsley, et al. (1993) *Neuromusc Disord* 3: 537–539.
12. Pasquini, et al. (1995) *Neuromusc Disord* 5: 105–114.
13. Passaquin, et al. (1993) *J. Neuroscience Res.* 35: 363–372.
14. Cross, et al. (1994) *Nat. Genet.* 6: 236–244.
15. Koike, et al. (1995) *Proc. Natl. Acad. Sci.* USA 92: 10624–10628.
16. Lederfein, et al. (1993) *Human Molecular Genetics* 2(11): 1883–1888.
17. Weintraub, et al. (1991) *Science* 251: 761–766.
18. Li, et al. (1993) *Journal of Biological Chemistry* 268(5): 3563–3572.
19. Love, et al. (1991) *Proc. Natl. Acad. Sci.* USA 88: 3243–3247.
20. Schofield, et al. (1993) *Developmental Dynamics* 198 (4): 254–264.
21. Moscoso, et al. (1995) *Molecular and Cellular Neuroscience* 6(1): 80–89.
22. Smale, et al. (1989) *Cell* 57: 103–113

We claim:

1. A nucleic acid isolate consisting of a promoter which comprises the sequence of nucleotides shown 5' to position 898 in SEQ ID NO: 1.

2. A nucleic acid construct comprising the promoter of claim 1 operably linked to a heterologous sequence.

3. The nucleic acid construct according to claim 2 wherein the heterologous sequence is a coding sequence.

4. The nucleic acid construct according to claim 3 wherein the heterologous sequence encodes a reporter molecule.

5. An isolated host cell comprising the nucleic acid construct according to claim 2.

6. A method comprising culturing the host cell according to claim 5 under conditions that result in transcription of said heterologous sequence from the promoter.

7. The method according to claim 6 wherein the heterologous sequence is a coding sequence and the host cell is cultured under conditions that result in expression of the encoded peptide or polypeptide product.

8. The method according to claim 6 further comprising detection of transcription of the heterologous sequence.

9. The method according to claim 7 further comprising detection of expression of the encoded peptide or polypeptide product.

10. A nucleic acid isolate consisting of a promoter which comprises the sequence of nucleotides shown 5' to position 853 of the mouse sequence shown in SEQ ID NO: 3.

11. A nucleic acid construct comprising the promoter of claim 10 operably linked to a heterologous sequence.

12. The nucleic acid construct according to claim 11 wherein the heterologous sequence is a coding sequence.

13. The nucleic acid construct according to claim 12 wherein the heterologous sequence encodes a reporter molecule.

14. An isolated host cell comprising the nucleic acid construct according to claim 11.

15. A method comprising culturing the host cell according to claim 14 under conditions for transcription of said heterologous sequence from the promoter.

16. The method according to claim 15 wherein the heterologous sequence is a coding sequence and the host cell is cultured under conditions that result in expression of the encoded peptide or polypeptide product.

17. The method according to claim 15 further comprising detection of transcription of the heterologous sequence.

18. The method according to claim 16 further comprising detection of expression of the encoded peptide or polypeptide product.

19. A nucleic acid isolate consisting of a promoter which comprises nucleotides numbered 746–898 in the sequence shown in SEQ ID NO: 1.

20. A nucleic acid construct comprising the promoter of claim 19 operably linked to a heterologous sequence.

21. The nucleic acid construct according to claim 20 wherein the heterologous sequence is a coding sequence.

22. The nucleic acid construct according to claim 21 wherein the heterologous sequence encodes a reporter molecule.

23. An isolated host cell comprising the nucleic acid construct according to claim 20.

24. A method comprising culturing the host cell according to claim 23 under conditions that result in transcription of said heterologous sequence from the promoter.

25. The method according to claim 24 wherein the heterologous sequence is a coding sequence and the host cell is cultured under conditions that result in expression of the encoded peptide or polypeptide product.

26. The method according to claim 24 further comprising detection of transcription of the heterologous sequence.

27. The method according to claim 25 further comprising detection of expression of the encoded peptide or polypeptide product.

* * * * *

UNITED STATES PATENT AND TRADEMARK OFFICE

CERTIFICATE OF CORRECTION

PATENT NO. : 5,972,609
DATED : October 26, 1999
INVENTOR(S) : TINSLEY et al

It is certified that error appears in the above-identified patent and that said letters patent is hereby corrected as shown below:

In the title, on face page, item [54], change the title to read as --UTROPHIN GENE PROMOTER--".

Signed and Sealed this

Twenty-fifth Day of July, 2000

Attest:

Q. TODD DICKINSON

*Attesting Officer*                *Director of Patents and Trademarks*

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1246 base pairs
      (B) TYPE: nucleic acid
      (C) STRANDEDNESS: double
      (D) TOPOLOGY: linear (xi) SEQUENCE DESCRIPTION: SEQ ID NO: 1:

```
AAGCTTGGAA CAGGCTCTAT AACAGATGTG CGTTTGTGTG TGCATATTGG AAAACAGAAA        60

AATAAGGTCA GCGCAAACAC TACTTGTAAT ACAAACTAAT GTAAGAGAAA ACTTCTTTTT       120

CAATATTAAC AACGACACTA GAGAAATAAT GTAAAATAAA TATACGGTTG GAACTAGGGG       180

TAAAAAAAAA ATCAGCAACG TCAGCAAACT GAGATGGGGT GAGTTGGAAG GCAGATTGGA       240

ATTTATCTCT TAACAAAATA TCACCCTAAC TAGAGACCTG TTTTGCCTAA GGGGACGTGA       300

CTCACATTTT CGGATAATCT GAATAAGGGG AATTGTGTCT GCTCGAGGCA TCCATTCTGG       360

TTCGGTCTCC GGACTCCCGG CTCCCGGCAC GCACGGTTCA CTCTGGAGCG CGCGCCCCAG       420

GCCAGCCAAG CGCCGAGCCG GGCTGCTGCG GGCTGGGAGG GCGCGCAGGG CCGGCGCTGA       480

TTGACGGGGC GCGCAGTCAG GTGACTTGGG GCGCCAAGTT CCCGACGCGG TGGCCGCGGT       540

GACCGCCGAG GCCCGGCAGA CGCTGACCCG GGAACGTAGT GGGGCTGATC TTCCGGAACA       600

AAGTTGCTGG GCCGGCGGCG GCGGGGCGAG AGCGCCGAGG GGGAGCCGGA GCGCTGCAGA       660

GGCGCGGGCC GGAGGGCTGG CGCTGATCTG CACCCTTCTC ATCTGGAGAG CGGACCCCTG       720

GCTGCCCGGA GGCGAGCCCC TTCCCGGGGG GTGGGGGCGG CAACGCGCGA CCCAGCGGTC       780

CTGCGCCCCA CCCTCCCTCC TCCGCCTCCA GCGCTCGGCT CCAACAAAGG GGCAGGCCCG       840
```

```
CAGCGGGGAG GAGGAGGAGG AGCCGCCGAA GGAGCGAGCC TCTCTCGCGC ACAAAGTTGT      900

GGAGTCGTTT TTCCTCGGAG CAGGGAAGCG GGCAGCAGCA GCCGGCCGCG GGCTTTCTCC      960

CGCCGAGGGG CGAGGAGGAG CCTCTGGCTC CAGAAGCCGA TTGGGGAATC ACGGGGAGCG     1020

GCGCCCCCCT TCTTTTGGGT CATTTCTGCA AACGGAAAAC TCTGTAGCGT TTGGCAAAGT     1080

TGGTGCCTGC GCGCCCCTTC CAGGTTTGCG CTTTGACTGT TTTGTTTTTG GCGGAACTAC     1140

CAGGCAGGAA GATTGCACAA GTAAGGGCG  TTTTCAGTCG GTGTCAATT  TCTCTTTCTT     1200

TCTTTCTTTT TTTAAAATTT CGGTTCGTGT CTGCTTCTCC AAGCTT                    1246
```

(2) INFORMATION FOR SEQ ID NO: 2:

(i) SEQUENCE CHARACTERISTICS:
        (A) LENGTH: 1655 base pairs
        (B) TYPE: nucleic acid
        (C) STRANDEDNESS: double
        (D) TOPOLOGY: linear (xi) SEQUENCE DESCRIPTION: SEQ ID NO: 2:

```
AAGCTTGGAA CAGGCTCTAT AACAGATGTG CGTTTGTGTG TGCATATTGG AAAACAGAAA       60

AATAAGGTCA GCGCAAACAC TACTTGTAAT ACAAACTAAT GTAAGAGAAA ACTTCTTTTT      120

CAATATTAAC AACGACACTA GAGAAATAAT GTAAATAAA  TATACGGTTG AACTAGGGG       180

TAAAAAAAAA ATCAGCAACG TCAGCAAACT GAGATGGGGT GAGTTGGAAG GCAGATTGGA      240

ATTTATCTCT TAACAAAATA TCACCCTAAC TAGAGACCTG TTTTGCCTAA GGGGACGTGA      300

CTCACATTTT CGGATAATCT GAATAAGGGG AATTGTGTCT GCTCGAGGCA TCCATTCTGG      360

TTCGGTCTCC GGACTCCCGG CTCCCGGCAC GCACGGTTCA CTCTGGAGCG CGCGCCCCAG      420

GCCAGCCAAG CGCCGAGCCG GGCTGCTGCG GGCTGGGAGG GCGCGCAGGG CCGGCGCTGA      480

TTGACGGGGC GCGCAGTCAG GTGACTTGGG GCGCCAAGTT CCCGACGCGG TGGCCGCGGT      540

GACCGCCGAG GCCCGGCAGA CGCTGACCCG GGAACGTAGT GGGGCTGATC TTCCGGAACA      600

AAGTTGCTGG GCCGGCGGCG GCGGGGCGAG AGCGCCGAGG GGGAGCCGGA GCGCTGCAGA      660

GGCGCGGGCC GGAGGGCTGG CGCTGATCTG CACCCTTCTC ATCTGGAGAG CGGACCCCTG      720

GCTGCCCGGA GGCGAGCCCC TTCCCGGGGG GTGGGGGCGG CAACGCGCGA CCCAGCGGTC      780

CTGCGCCCCA CCCTCCCTCC TCCGCCTCCA GCGCTCGGCT CCAACAAAGG GGCAGGCCCG      840

CAGCGGGGAG GAGGAGGAGG AGCCGCCGAA GGAGCGAGCC TCTCTCGCGC ACAAAGTTGT      900

GGAGTCGTTT TTCCTCGGAG CAGGGAAGCG GGCAGCAGCA GCCGGCCGCG GGCTTTCTCC      960

CGCCGAGGGG CGAGGAGGAG CCTCTGGCTC CAGAAGCCGA TTGGGGAATC ACGGGGAGCG     1020

GCGCCCCCCT TCTTTTGGGT CATTTCTGCA AACGGAAAAC TCTGTAGCGT TTGGCAAAGT     1080

TGGTGCCTGC GCGCCCCTTC CAGGTTTGCG CTTTGACTGT TTTGTTTTTG GCGGAACTAC     1140

CAGGCAGGAA GATTGCACAA GTAAGGGCG  TTTTCAGTCG GTGTCAATT  TCTCTTTCTT     1200

TCTTTCTTTT TTTAAAATTT CGGTTCGTGT CTGCTTCTCC AAGCTTTATT TTTTTTTAA     1260

AATACATCGC ACCACCAAAC TAACACTCGC ACACACCCCC GCGGTTACTC CGTGTCAAAC     1320

TCCTAGAGGA GCCCTTGGCC AGCTCGGGGT GCGGCGGTGG CGACCGGCAG GCGAGGAGGC     1380

CCGCGGGCAG CAGGTAAGCC CATGCATTAT TGAAGCCTCG GGCTGGTAAT GTGACTACAG     1440

CCCCCGAGGG AATGGGGCGG GGGCCGGGAG GAGGATGGCT CTTTCTGCGG TTCTTCCGCC     1500

TGGGATCGGC GTCCCGAGCT GCTTCCCAAG TCCCAGAGTC GAAGATGGGA GTAACTTTTG     1560

CGTGCCCTTT CCTCGGGGCC TCAGTTTAGC TCCCCGCGGT GCGAGAGAGA ATGCCGGAGG     1620
```

-continued

```
CGTGGAGAGC TCGGGCGTGG AGGTCCTTGG GATCC                         1655
```

(2) INFORMATION FOR SEQ ID NO: 3:

(i) SEQUENCE CHARACTERISTICS:
        (A) LENGTH: 1528 base pairs
        (B) TYPE: nucleic acid
        (C) STRANDEDNESS: double
        (D) TOPOLOGY: linear (xi) SEQUENCE DESCRIPTION: SEQ ID NO: 3:

```
CACCAGCACC CCAAATACAC ACAACACACA CACACACACA CACACACACA CACACACACA    60
CACACACACG GTAAAAATTT TAAAGGTCAG CACCAACACT ATTTGTGTAT ATGAACATAT   120
AAGGACACTT GGGATTGTTT AGACAGCATT TAAAATGATC CAAAGAAAAT TCCATAAAAT   180
AAATATACCC CTGGATTTAG AACCCCAAAC TCAACAACCT CAGTAAACTG AAATGGGGCG   240
AATTGGCCAG AAGGTTGAGA TTTATATAAG ATAATAATAA AAAAAAATTA AAAGTACTGT   300
TGATAAGAGA CCTAGTGTGC CTAGAGGGGT GTGACACACA TTTTCGGACA ATTTGAATAA   360
AGGGCACGGT GCGTGCGCGC GGTGACTATT CCAGCTTCTG GCTTCCAGCA CGCACGACTG   420
GTTCCGGGAT TCTCGCACCG CGCACCGCAC GGAGCCGGCT GCTGCGGGCT GGGAGGGCGC   480
CTAGGGCTAG CGCTGATTGA CCGGGCGCGC GGTCAGGTGA CCCGAAGCGC CACGTTCTGG   540
GAGCCCGGCC CGCGGTGGCT TCCCAGGCCG GGGCAGGACC GAACCCGGAG CCGAGGGGGA   600
CTGGTCTCCC CGGGAGAACA AAGTTGCCCG GCCTGGGGCC CCGGGGCGCG CGAGCGGCGA   660
GACGGCGGGT CCGACCTGCG GGATCCACGG TTCCGAGGTT GGGTGATTCG TGCTGGGAGA   720
CGCGAGCCCC TACCCGGGGT GGCGGGCGGA CCCAGCAGCG CCCCACCCTC GTTCTCCAAC   780
AAAGGGGCCG GCGGAAGCCG GAGGAGGACC TGGAGGAGGA GCCGGAGCGG CGAGCAGCTC   840
TCGCGCACAA AGTTGTGGAG TCGCCCTTCC CCCGACGAGG GGAGCGGGCA GCGCCGGGCG   900
CGGGATTTCT CCCGCCCAGG GCCGAGGAGG AGCCCTGGGC TCCTCAGCCG ATCGGGCCAC   960
CTCGGGGAGC GGCGCCCCTT TTCTTTCGGG TCATTCCTGC AGAGGGAAAA CTCCTGCGTG  1020
CGCCTGCCCC CAGGCTAGCG TTTGGACTGT TTTGTTTTTG GCGGAACTAC CGGGCAGGAA  1080
GATTGCACAA GTCAGGGGGC GTTTCCAATC GGGTGTCAAT TTTGGATCTC CCCCCCCCA   1140
ACCCCCCTTT GGATCTTGTC GGGCTTTCCA CGTTTCACTT AAAAAAAATT CTTGTAACGT  1200
CCAAGGCAAG CTCCCCACCA CCCGAACACG CCCAGAGGAA CCTTGGGGCC TCTGGGACTT  1260
GGCTAGCAGG TAAGCCCATG CATTATTGAA GCTTCGGTCT GGGTAATGTG ACCGCAGTCC  1320
CCTAGGGAAT GGGGCGGGGG TTGAAAGGAG GTGGGACCTT TCTGCAGTTC CACCGCCCGG  1380
GTCCCGAAGT AGCTGTAGCC AACTTCTGCA CTTTCCCTGG AAGCTCAGCG TCCCCTGCCT  1440
GGGCGGGAGA GAGCTGGGTT GAGAAGGTGG GAATCTGTAC TGGTCGCCAC GGTCTCAGAT  1500
TCCTAGGTCT AGTTTAGTAC TGTTGTTT                                    1528
```